United States Patent
Horn et al.

(10) Patent No.: US 8,245,740 B2
(45) Date of Patent: Aug. 21, 2012

(54) FRACTION COLLECTOR

(75) Inventors: Marcus J. Horn, Parsippany, NJ (US);
Blaine Marsh, Columbia, NJ (US)

(73) Assignee: Alfa Wassermann, Inc., West Caldwell, NJ (US)

(*) Notice: Subject to any disclaimer, the term of this patent is extended or adjusted under 35 U.S.C. 154(b) by 1295 days.

(21) Appl. No.: 11/916,307

(22) PCT Filed: Jun. 3, 2005

(86) PCT No.: PCT/US2005/019586
§ 371 (c)(1),
(2), (4) Date: Dec. 3, 2007

(87) PCT Pub. No.: WO2006/132620
PCT Pub. Date: Dec. 14, 2006

(65) Prior Publication Data
US 2008/0190829 A1    Aug. 14, 2008

(51) Int. Cl.
*B65B 43/42* (2006.01)
(52) U.S. Cl. ........ 141/130; 141/231; 141/232; 141/233; 141/284; 422/500; 422/501
(58) Field of Classification Search .......... 141/130, 141/284, 234–237, 231–233; 422/99, 100, 422/500–507
See application file for complete search history.

(56) References Cited

U.S. PATENT DOCUMENTS

| | | | |
|---|---|---|---|
| 3,168,124 A * | 2/1965 | Lenkey | 141/284 |
| 3,477,478 A * | 11/1969 | Robertson et al. | 141/284 |
| 4,140,018 A * | 2/1979 | Maldarelli et al. | 73/863.11 |
| 4,199,013 A * | 4/1980 | Reich et al. | 141/130 |
| 5,055,263 A * | 10/1991 | Meltzer | 422/65 |
| 5,443,791 A * | 8/1995 | Cathcart et al. | 422/65 |
| 5,942,441 A * | 8/1999 | Nylen | 436/179 |
| 5,988,236 A * | 11/1999 | Fawcett | 141/130 |
| 6,006,800 A * | 12/1999 | Nakano | 141/130 |
| 6,589,483 B1 * | 7/2003 | Maeda | 422/525 |
| 7,095,032 B2 * | 8/2006 | Montagu et al. | 250/458.1 |
| 7,168,391 B2 * | 1/2007 | Gudmundsson et al. | 119/14.18 |

FOREIGN PATENT DOCUMENTS

JP    59040145    3/1984
(Continued)

OTHER PUBLICATIONS

Japanese Office Action (with English translation) dated Oct. 5, 2010 application No. 2008-514611.

(Continued)

*Primary Examiner* — Timothy L Maust
(74) *Attorney, Agent, or Firm* — Ohlandt, Greeley, Ruggiero & Perle, LLP

(57) ABSTRACT

A device for positioning a component thereof along x- and y-axes of the device is provided. The device includes first and second motors, a carriage containing the component to be positioned, a lead screw to position the carriage along a first axis of the device, and a keyed shaft to position component to be positioned along a second axis of the device. The first motor drives the lead screw and the second motor drives the flatted shaft. In some embodiments described herein, the flatted shaft turns a first pulley, which is connected to a second pulley by a belt. The component to be positioned is attached to the belt and moves along a second axis of the device as the belt moves.

26 Claims, 5 Drawing Sheets

FOREIGN PATENT DOCUMENTS

| | | |
|---|---|---|
| JP | 11304818 | 11/1999 |
| JP | 2000306159 | 11/2000 |
| JP | 2001033463 | 2/2001 |

OTHER PUBLICATIONS

International Search Report and Written Opinion dated Oct. 12, 2005 in corresponding International Application No. PCT/US2005/19586.

International Preliminary Report on Patentability dated Nov. 30, 2010 in corresponding International Application No. PCT/US2005/19586.

Japanese Final Office Action dated Oct. 25, 2011 in corresponding application No. 2008-514611 with English translation.

* cited by examiner

FRACTION COLLECTOR

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

BACKGROUND OF THE INVENTION

The present invention relates generally to the art of fraction collectors, and more specifically to an X-Y fraction collector with minimal moving wires or motors and minimized energy usage.

Fraction collectors are commonly used for collecting liquid fractions originating from a chromatography column or other separation means, where the composition of the liquid varies with time as the liquid emerges from the separation means. Typically, a fraction collector includes a plurality of tubes to receive fractions of the liquid sample, as well as a dispensing means by which the liquid sample fractions are directed into various tubes. The fraction collector is adapted to dispense discrete fractions of the liquid sample into individual tubes so that the fractions, or contents thereof, can be recovered for further use.

Known fraction collectors typically have one of two configurations. So-called "X-Y collectors" utilize a rectangular arrangement of tubes and the dispenser moves in a rectilinear fashion, dispensing fractions into individual tubes. In the second configuration, the tubes are located on a circular turntable, which rotates as the fractions are being dispensed, thereby presenting a separate tube to the dispenser for each desired fraction to be dispensed.

Although both configurations of fraction collector described above are commonly used, each suffers from disadvantages as currently known in the art. While turntable-style fraction collectors are useful, there are instances in which an X-Y collector is preferable. For example, use of an X-Y collector preserves valuable bench space as compared to a turntable collector when a large number of tubes are being filled. Further, commonly used receptacles such as microtitre plates have wells that are generally arranged in a rectangular X-Y pattern. A turntable collector cannot effectively dispense samples into such receptacles.

Disadvantages also exist with respect to X-Y collectors. For example, X-Y collectors generally require the movement of wires as the dispenser moves over a microtitre plate or series of tubes. This movement can lead to breakage of the wires, especially as they lose their elasticity and become more brittle over time. Further, the carriage of such a dispenser generally includes a motor that must be moved along a first axis so that the dispenser can be moved along a second axis once it is properly positioned on the first axis. Movement of portions of the fraction collector having motors located thereon can lead to misalignment of the motor and also increases the load on the motor used to position the carriage, leading to greater energy consumption and an increased likelihood of failure on the part of that motor.

What is needed, therefore, is a fraction collector with fine movement control along its axes, a lack of moving wires or motors, and minimized energy consumption.

BRIEF SUMMARY OF THE INVENTION

The present invention is directed to a device for positioning a component thereof along x- and y-axes of the device. The device includes first and second motors, a carriage containing the component to be positioned, a lead screw to position the carriage along a first axis of the device, and a keyed shaft to position component to be positioned along a second axis of the device. The first motor drives the lead screw and the second motor drives the keyed shaft. In some embodiments described herein, the keyed shaft turns a first pulley, which is connected to a second pulley by a belt. The component to be positioned is attached to the belt and moves along a second axis of the device as the belt moves. The term "keyed" as used herein in reference to the keyed shaft of the present invention includes a flatted shaft, as described below, as well as a slotted shaft or any other shaft wherein the configuration of the shaft corresponds to a configuration of a first pulley (as described below) such that rotation of the keyed shaft results in rotation of the first pulley.

A preferred embodiment of the present invention is directed to a fraction collector, wherein the component to be positioned is a dispenser. The fraction collector preferably has a rear portion, which holds the two motors and also has through-holes for the lead screw and flatted shaft, a first forward support portion having a through-hole for the lead screw, a second forward support portion having a through-hole for the flatted shaft, and a base portion to provide added stability to the device. In another preferred embodiment, the fraction collector includes a support shaft parallel to the lead screw, and the rear portion and forward support portion have additional through-holes to accommodate the support shaft. In this embodiment, the carriage has a through-hole to accommodate the support shaft and is slidably engaged therewith.

In another aspect of the present invention, two sensor assemblies are provided. The first sensor assembly is adapted to determine the extent of rotation of the lead screw so that the device can determine the extent of movement of the carriage (and thus the dispenser) along a first axis. The second sensor assembly is adapted to determine the extent of rotation of the flatted shaft so that the device can determine the extent of movement of the dispenser along a second axis.

In a preferred embodiment of the present invention, both sensor assemblies include encoder discs attached to the lead screw (in the case of the first sensor assembly) or the flatted shaft (in the case of the second sensor assembly). The sensor assemblies also include optical sensors that can determine the extent of rotation of the encoder disc, and therefore the extent of rotation of the lead screw or flatted shaft.

In a preferred embodiment, the present invention further includes a waste receptacle into which excess or unwanted sample can be dispensed.

In another embodiment, the dispenser of the present invention is adapted to extract as well as deliver sample, such that sample can be transferred by the device from one receptacle to another.

DETAILED DESCRIPTION OF THE INVENTION

Figure 1:
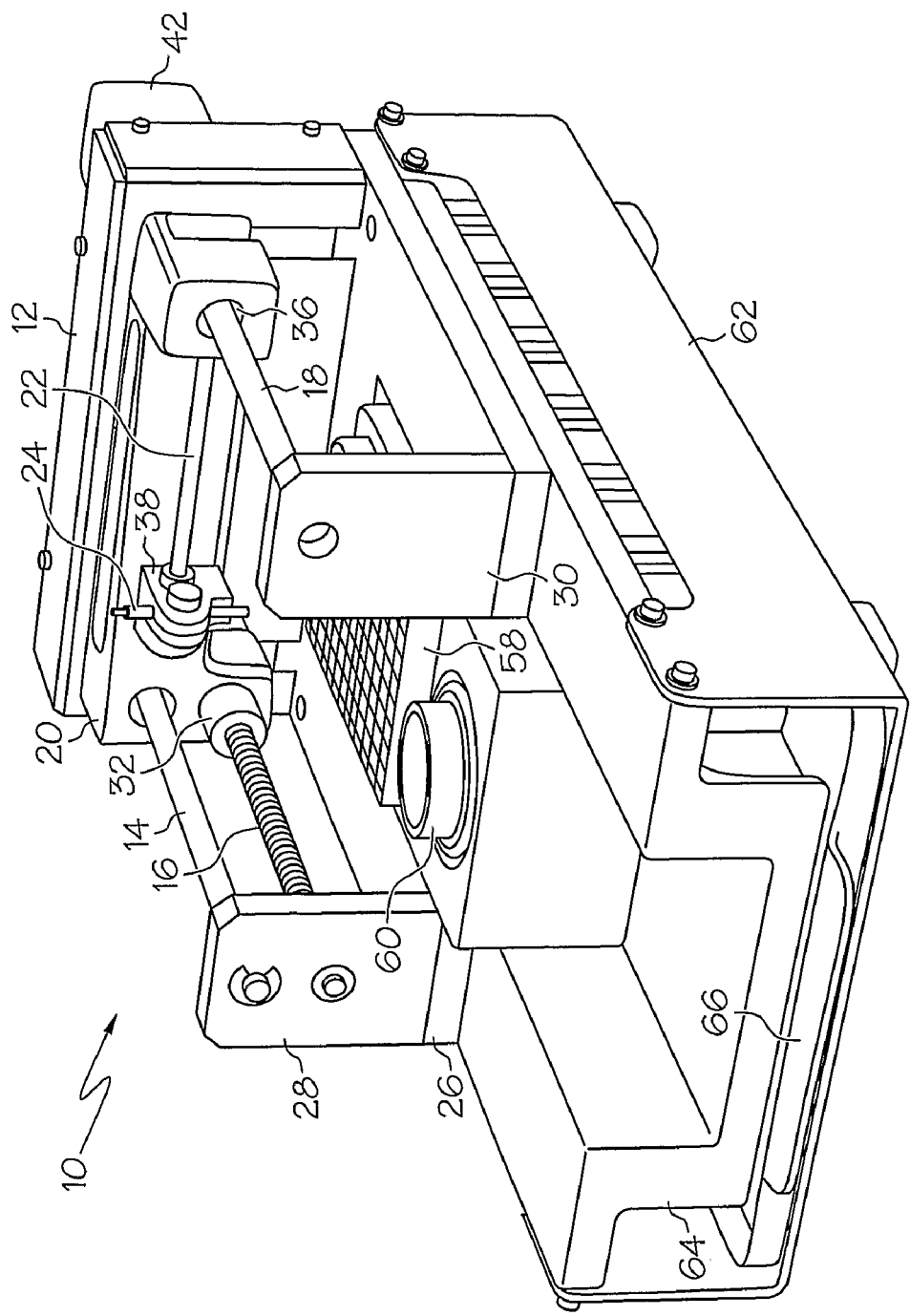
FIG. 1 is a front perspective view of a fraction collection assembly constructed in accordance with the teachings of the present invention.

Referring now to the drawings, wherein like numerals represent like parts, FIG. 1 is a front perspective view of a fraction collector 10 constructed in accordance with the teachings of the present invention. Fraction collector 10 includes a rear support 12 to which support shaft 14 is fixedly attached. Support shaft 14 extends from rear support 12 to a first forward support 28, to which support shaft 14 is also fixedly attached. Base portion 26 provides additional support to the device. As shown in FIG. 1, rear support 12 includes plates that shield portion of device 10, such as optical sensors (described below), from damage due to dripping and the like. These plates are not shown in FIGS. 2-5, as they would obscure other features of the device. The inclusion of these plates in the device of the present invention is optional.

Rotatably attached to rear support 12 is lead screw 16. Lead screw 16 is coupled to a drive means such as a first motor 40 (shown in FIG. 2). Motor 40 provides power to rotate lead screw 16, thereby moving a carriage 20 along a y-axis. Carriage 20 has a threaded through-hole (not shown) through which lead screw 16 passes such that the turning of lead screw 16 in either a clockwise or counterclockwise manner causes carriage 20 to move either forward or backward along a y-axis. The pitch of lead screw 16 determines the sensitivity with which carriage 20 can be moved along lead screw 16. The pitch of lead screw 16 can vary over a wide range, and any pitch suitable for a given purpose may be used. By way of example, the pitch may vary from about 0.8 mm to about 30 mm. In one aspect of the present invention wherein fraction collector 10 is used in conjunction with a 384-well plate, a pitch of about 3 mm is preferred. If a 96-well plate is used in place of a 384-well plate, the pitch of lead screw 16 is preferably increased to about 9 mm. Alternatively, to allow a greater degree of fine control in instances where a receptacle such as a microtitre plate has a greater number of wells, such as for example a 1536-well plate, the pitch of lead screw 16 is preferably reduced to about 1.0 mm or even to about 0.8 mm. Even though the above-cited pitch values are preferred in given instances, even for the receptacles described above other pitch values may be suitable. The present invention contemplates the use of any suitable pitch value, regardless of whether that value is specifically set forth herein.

A flatted shaft 18 is rotatably attached to rear support 12 and extends through a second through-hole 36 of carriage 20. Flatted shaft 18 extends forward to a second forward support 30, to which it is also rotatably attached. Flatted shaft 18 is coupled to a drive means, such as a second motor 42, which provides power to rotate flatted shaft 18, thereby moving dispenser 24 along an x-axis. Carriage 20 includes a support shaft 22 fixedly attached thereto. Support shaft 22 is oriented in a perpendicular fashion as compared to support shaft 14 and flatted shaft 18, such that if support shaft 14 and flatted shaft 18 can be said to define a y-axis of device 10, support shaft 22 defines an x-axis of device 10. Dispenser 24 is removably attached to a carrier 38, which is in turn slidingly attached to support shaft 22. When flatted shaft 18 is rotated in a clockwise or counterclockwise manner, carrier 38 is moved back and forth along an x-axis, as described below, thereby positioning dispenser 24 along that axis.

Carriage 20 of fraction collector 10 is adapted to move along a y-axis of device 10 by traveling along the length of lead screw 16. Lead screw 16 passes through a threaded bore (not shown) of carriage 20 such that when lead screw 16 is rotated in a clockwise or counter-clockwise direction, the action of lead screw 16 against threaded bore 32 of carriage 20 results in a corresponding backward or forward movement of carriage 20 along the length of lead screw 16. Carriage 20 carries dispenser 24, so that the motion of carriage 20 along a y-axis of device 10 is equivalent to a motion of dispenser 24 along a y-axis of device 10. Dispenser 24 is attached to a carrier 38, which is able to move along the length of a support shaft 22 along an x-axis of device 10. The movement of carrier 38, and therefore dispenser 24, along support shaft 22 is controlled by the rotation of flatted shaft 18.

Figure 3:
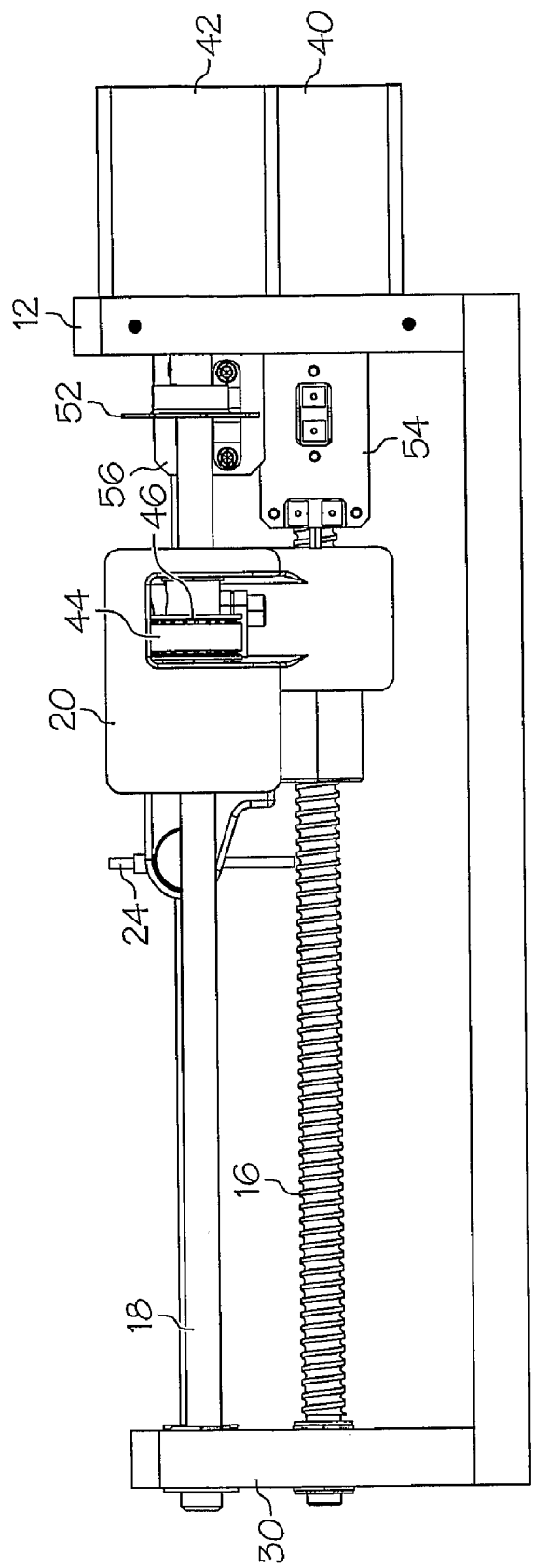
FIG. 3 is a left side plan view of a fraction collector constructed in accordance with the teachings of the present invention.

As best seen in FIG. 3, flatted shaft 18 extends through a first pulley 46 in a keyed manner, that is, such that the flatted configuration of flatted shaft 18 meshes with a corresponding configuration of first pulley 46. When flatted shaft 18 is rotated in a clockwise manner, the rotation causes a corresponding turning of first pulley 46 in the same direction. Likewise, when flatted shaft 18 is rotated in a counter-clockwise direction, the rotation of first pulley 46 matches that directional rotation of flatted shaft 18. In the embodiment of device 10 shown in the Figures, a D-shaped flatted shaft 18 is used, but it is contemplated that any suitable keyed shaft may be used.

As best shown in FIG. 3, first pulley 46 is operably associated with a second pulley 48 by means of a belt 44. Thus, when first pulley 46 is turned in either a clockwise or counter-clockwise direction by the rotational action of flatted shaft 18, belt 44 translates that movement to second pulley 48 such that second pulley 48 turns in a corresponding manner. Belt 44 is preferably a sturdy, treaded structure that can be controlled with precision by the turning of first and second pulleys 46 and 48. It is preferred that first and second pulleys 46 and 48 have grooves adapted to receive the treads of belt 44. Belt 44 is preferably constructed from a high-grade rubber or synthetic polymer, though it is contemplated that any suitable material may be used in its construction.

The rotation of flatted shaft 18 is preferably driven by a second motor 42 coupled thereto. Second motor 42 is preferably a stepper motor, though any suitable motor may be used.

Dispenser 24 is adapted to receive tubing (not shown) at an upper end thereof. The tubing provides a sample fluid to dispenser 24 to be dispensed into a receptacle such as a microtitre plate 58. The fluid sample may come from a centrifuge, a chromatography column, or from any other source. Although in a preferred embodiment the sample is provided to dispenser 24 using flexible tubing that can move along x- and y-axes of device 10 along with carriage 20, any suitable method of transmitting the sample, including the use of metal tubing, may be utilized. So long as the structure that provides sample to dispenser 24 is able to move with the motion of dispenser 24 along the x- and y-axes of device 10, then it may be suitable for use with device 10 in any given application.

Figure 2:
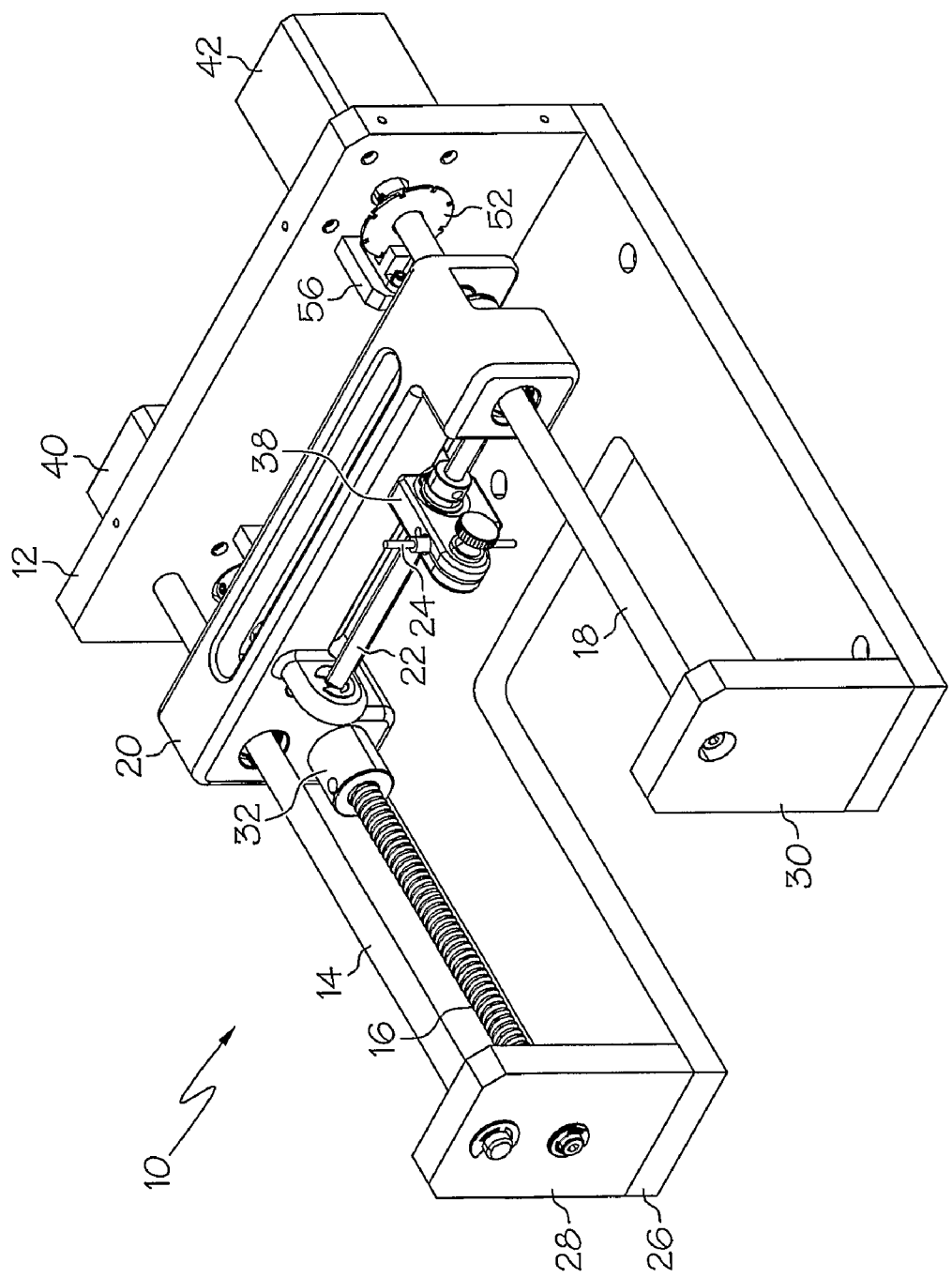
FIG. 2 is a top left perspective view of a fraction collector constructed in accordance with the teachings of the present invention.
Figure 4:
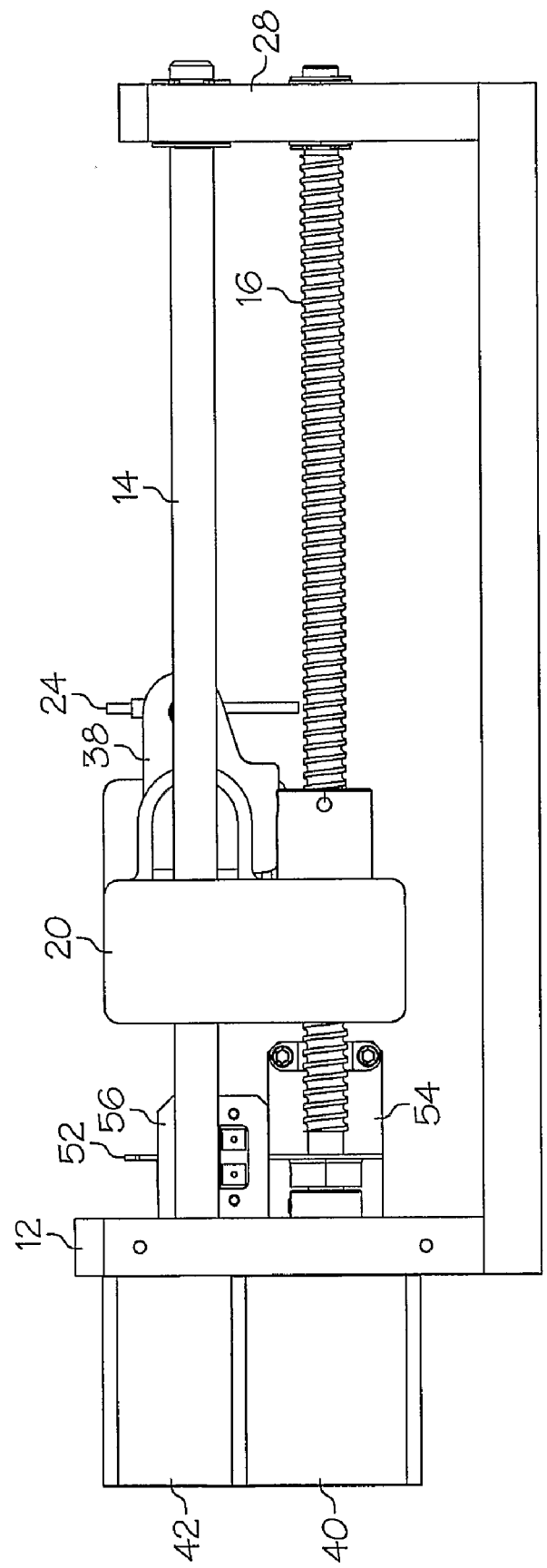
FIG. 4 is a right side plan view of a fraction collector constructed in accordance with the teachings of the present invention.
Figure 5:
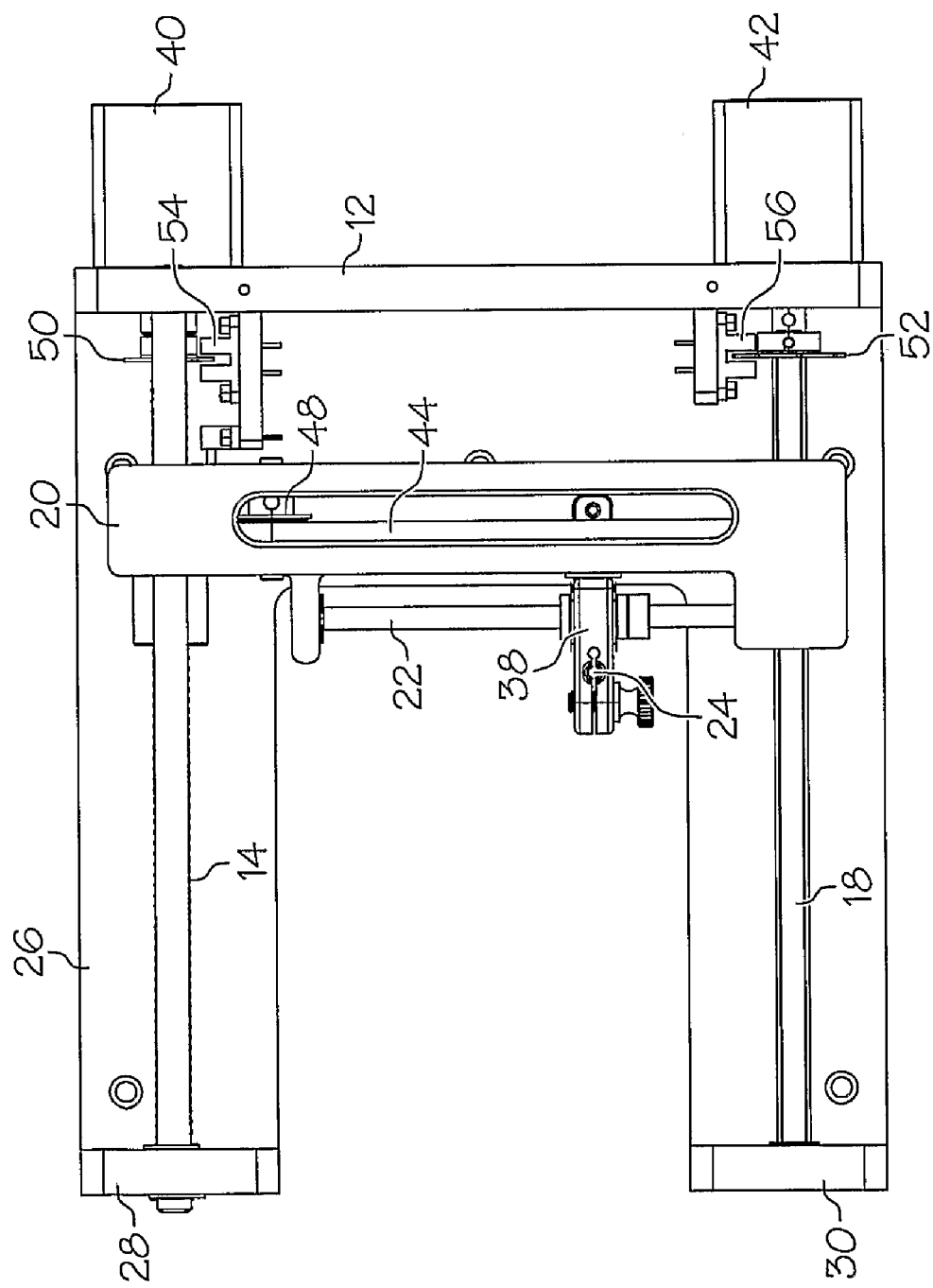
FIG. 5 is a top plan view of a fraction collector constructed in accordance with the teachings of the present invention.

In order to accurately dispense liquid fractions from dispenser 24 into a receptacle such as microtitre plate 58, it is necessary that device 10 include a method of determining the position of dispenser 24 along the x- and y-axes thereof. In a preferred embodiment of device 10, as best shown in FIGS. 2, 4 and 5, both lead screw 16 and flatted shaft 18 are coupled to encoder discs 50 and 52, which rotate along with the motion of lead screw 16 and flatted shaft 18, respectively. Encoder discs 50 and 52 include cutout portions along a perimeter thereof. Adjacent first encoder disc 50 is a first optical sensor 54. First optical sensor 54 is adapted to detect whether a cutout portion of encoder disc 50 has rotated into its field of view. Using this information, along with the circumference of encoder disc 50 and the placement of the cutout portions along the perimeter thereof, device 10 can determine the extent of rotation of lead screw 16, and thereby the amount of movement of carriage 20 either forward or backward along a y-axis of device 10. The combination of an optical sensor and an encoder disc may be referred to herein as a sensor assembly.

FIG. 1 depicts support structures 62 and 64, as well as drainage tray 66. These aspects of the present invention may be included with device 10 in some embodiments of the present invention, such as when the device is being used as a stand-alone device. FIGS. 2-5 do not show these features of the present invention, and in many application these structures will not be used. In any application for which the present device is suited, the use of these structures is optional.

Heretofore, the general structure of one embodiment of device 10 has been described. Now the operation of device 10 will be detailed. Specifically, the operation of an embodiment of device 10 as shown in the Figures will be detailed. The underlying inventive concept of the present invention is, however, susceptible to a variety of embodiments, and the general description of the operation of the embodiment of device 10 shown in the Figures is applicable to other embodiments of device 10, whether those that are described herein or those that will be readily apparent to one of skill in the art upon reading this disclosure.

The embodiment of device 10 shown in the Figures is adapted for use with a 96-well microtitre plate, as shown in FIG. 1. A fluid sample from a sample source such as, for example, a centrifuge or chromatography column, is directed to an upper end of dispenser 24. The fluid sample travels through dispenser 24 and emerges from a lower end thereof to enter a well in microtitre plate 58. Device 10 is preferably in electronic communication with a computer (not shown) into which a user has inputted retention times for various fractions of sample to be dispensed into the wells of microtitre plate 58. The user may also input into the computer the order of wells into which the sample fractions are to be dispensed. Dispenser 24 is, then, positioned over the correct well of 96-well microtitre plate 58 at the appropriate time such that the correct sample fraction will be dispensed into the correct well. Further, the time period for which dispenser 24 is positioned over a given well is provided so that an entire fraction, or some portion thereof, may be provided to a specific well. By use of optical sensors 54 and 56, and encoder discs 50 and 52, as described above, device 10 is able to determine the precise position of dispenser 24 with respect to microtitre plate 58 in order to ensure that each sample fraction is delivered to the correct well. Further, use of optical sensors 54 and 56, in conjunction with encode discs 50 and 52, ensures that device 10 is able to ascertain whether dispenser 24 has, in fact, moved, reducing error due to situations in which, for example, a signal is sent to one of first and second motors 40 and 42 to rotate lead screw 16 or flatted shaft 18, but due to a failure in the system, carriage 20, and therefore dispenser 24, has not actually moved. Since device 10 knows the position of dispenser 24 at any given time, device 10 will also be able to provide to a user information concerning which well contains any erroneously-dispensed sample.

In addition to relying on user input of retention times, device 10 may dispense in accordance with times (and volumes dispensed) determined by other suitable methods, including manual operation, sensors that determine volume, or absorbance readings taken from said sample. Any of a number of other methods known in the art may be used.

At various times during acquisition of sample, it may be desirable to dispose of a quantity of the fluid sample delivered to dispenser 24. In such an instance, device 10 is able to dispense the sample into waste receptacle 60 using the same method of moving dispenser 24 and determining the position thereof as described above. Thus, any portion of the sample that is desired to be discarded need not occupy any of the limited number of wells in microtitre plate 58.

The present device may be operably associated with a computer into which a user can input certain information, such as the type or number of receptacles into which sample is to be dispensed, and the order of dispensing the sample. For example, the user may program the device to dispense sample sequentially along an x-axis of the receptacle or group of receptacles, or the user may program the device to dispense sample sequentially along a y-axis of the receptacle or group of receptacles. The user may program the device to dispense sample into every receptacle (or every well of a microtitre plate) as it passes along a given axis, or to skip one or more receptacles or wells. In addition, the user can program the device to dispense sample into one receptacle for a greater period of time than the next. Any degree of customization a user may desire in terms of order or configuration of sample dispensed, or retention times dispensed into given receptacles, may be programmed by the user.

It is contemplated that the present invention is not limited in terms of materials used in its construction. Various shafts, for example, may be constructed of stainless steel or aluminum, or any other suitable material. Likewise, the base, rear portion, and forward support portions may be constructed from metals or other suitable materials such as carbon fiber. If the present device is intended for use with certain chemical applications, then the nature of the chemicals used may dictate the materials used in certain components of the present invention. The materials that may be used in any given application will be apparent to those of skill in the art. It is contemplated herein that any suitable materials may be used in construction of any of the various portions of the present invention.

Certain details concerning the various components of the fraction collector, such as how to mount them, the use of ball bearings, and the like, are not described herein. It will be obvious to those of skill in the art, upon reading this disclosure, that various designs of the individual components of the present fraction collector are possible. Further, electric and electronic driving circuits are not described in detail because it is well-known how to control stepper motors and the like. The same is true of any software components that may be used in various aspects of the present invention. Once the present invention is understood, providing software in various forms to control the operation of the device is something that can be readily achieved by those skilled in the art.

It will be obvious to those of skill in the art upon reading this disclosure that many variations of the present invention are possible without departing from the spirit or scope of the invention described herein. Such variations include, but are not limited to, the type of driving means for various moving shafts, the location and position of various motors, and shafts. By way of example, and not by way of limitation, the flatted shaft and the support shaft of the present device may be exchanged in terms of relative position. Further, the positions of the lead screw and the support shaft might be switched without departing from the scope of the invention. An extended threaded nut 32 may be added to carriage 20 for passage of lead screw 16 therethrough in order to increase resolution along a y-axis of the device. Further, a single lead screw and support shaft could be placed in the center of a device to control a dual-carriage, one extending in either direction from the lead screw and support shaft, such that the operations of the present device are performed in tandem. Devices as described herein may also be placed in tandem, one in front of the other, and controlled by the same extended lead screw and flatted shaft. The number and kind of modifications that may be made to the present device are varied and large, and it is contemplated that such modifications are within the scope of the present invention. The specific embodiments described herein are given by way of example only, and the present invention is limited only by the appended claims.

The invention claimed is:

1. A device for positioning a component thereof along x- and y-axes comprising:
   a first motor;
   a lead screw coupled to said first motor and extending along a first axis of said device;
   a second motor;
   a keyed shaft coupled to said second motor and extending along said first axis of said device;
   a carriage portion threadably engaged with said lead screw for movement along a length thereof, said carriage portion further slidingly engaged with said keyed shaft for movement along a length thereof;
   a shaft portion fixedly attached to said carriage portion and defining a second axis of said device, said second axis being perpendicular to said first axis;
   a positionable portion to be positioned along said first and second axes of said device, said positionable portion being slidingly attached to said shaft portion, wherein said positionable portion is operably coupled to said keyed shaft such that rotation of said keyed shaft causes movement of said positionable portion along a length of said shaft portion;
   a first sensor assembly coupled to said lead screw for determining the extent of rotation thereof; and
   a second sensor assembly coupled to said keyed shaft for determining the extent of rotation thereof.

2. A device according to claim 1 wherein said positionable portion comprises a dispenser for dispensing a fraction of a fluid sample into a receptacle.

3. A device according to claim 1 further comprising a support shaft parallel to said lead screw, wherein said carriage portion is slidably engaged with said support shaft for movement along a length thereof.

4. A device according to claim 3 wherein said positionable portion comprises a dispenser for dispensing a fraction of a fluid sample into a receptacle.

5. A device according to claim 1 wherein said first sensor assembly comprises a first encoder disc fixedly attached to said lead screw and a first optical sensor for determining the extent of rotation of said first encoder disc, and wherein said second sensor assembly comprises a second encoder disc fixedly attached to said keyed shaft and a second optical sensor for determining the extent of rotation of said second encoder disc, wherein said device is able to determine the position of said positionable portion along said first and second axes based upon the extent of rotation of said first and second encoder discs.

6. A device according to claim 5 wherein said positionable portion comprises a dispenser for dispensing a fraction of a fluid sample into a receptacle.

7. A device according to claim 1 further comprising a rear portion to which said first and second motors are fixedly attached, said rear portion having a first through-hole through at least a portion of which said lead screw extends, and said rear portion further having a second through-hole through at least a portion of which said keyed shaft extends.

8. A device according to claim 7 further comprising a support shaft parallel to said lead screw, wherein said carriage portion is slidably engaged with said support shaft for movement along a length thereof, and wherein said rear portion has a third through-hole through which at least a portion of said support shaft extends.

9. A device according to claim 8 further comprising a first forward support having a first through-hole through at least a portion of which said lead screw extends, said first forward support further having a second through-hole through at least a portion of which said support shaft extends, said first forward support being portioned at a distal end of said lead screw and a distal end of said support shaft with respect to said rear portion.

10. A device according to claim 9 further comprising a second forward support having a through-hole through at least a portion of which said keyed shaft extends, said second forward support being positioned at a distal end of said keyed shaft with respect to said rear portion.

11. A device according to claim 10 further comprising a base portion fixedly attached to said rear portion and extending away therefrom, said base portion also fixedly attached to said first and second forward support portions.

12. A device according to claim 2 wherein said dispenser is adapted to extract a fluid sample from a receptacle in addition to delivering a fluid sample thereto.

13. A device according to claim 12 further comprising:
   a first pulley operably associated with said keyed shaft such that rotation of said keyed shaft causes a corresponding rotation of said first pulley;
   a belt portion operably associated with said first pulley such that rotation of said first pulley causes a corresponding movement of said belt; and
   a second pulley operably associated with said belt such that movement of said belt causes a corresponding rotation of said second pulley,
   wherein said positionable portion is fixedly attached to said belt portion such that movement of said belt portion causes a corresponding movement of said positionable portion.

14. A fraction collector comprising:
   a rear portion having a first through-hole and a second through-hole;
   a first motor fixedly attached to said rear portion;
   a lead screw extending through at least a portion of said first through-hole of said rear portion and rotatably attached to said rear portion, and extending along a first axis of said fraction collector, said lead screw further being coupled to said first motor;
   a second motor fixedly attached to said rear portion;
   a flatted shaft extending through at least a portion of said second through-hole of said rear portion and rotatably attached to said rear portion, and extending along a first axis of said fraction collector, said flatted shaft further being coupled to said second motor;
   a carriage portion having a threaded bore threadably engaged with said lead screw for movement along a length thereof, said carriage portion further having a first carriage through-hole slidably engaged with said flatted shaft for movement along a length thereof;

a shaft portion fixedly attached to said carriage and defining a second axis of said fraction collector, said second axis being perpendicular to said first axis;

a positionable portion to be positioned along said first and second axes of said fraction collector, said positionable portion being slidingly attached to said shaft portion and operably coupled to said keyed shaft such that rotation of said keyed shaft causes movement of said positionable portion along said shaft portion, said positionable portion comprising a dispenser for dispensing a fraction of a fluid sample into a receptacle;

a first sensor assembly comprising a first encoder disc fixedly attached to said lead screw and a first optical sensor for determining the extent of rotation of said lead screw;

a second sensor assembly comprising a second encoder disc fixedly attached to said flatted shaft and a second optical sensor for determining the extent of rotation of said flatted shaft; and a base portion fixedly attached to said rear portion and extending away therefrom, said base portion also fixedly attached to said first and second forward support portions.

15. A fraction collector according to claim 14 further comprising:

a first pulley operably associated with said flatted shaft such that rotation of said flatted shaft causes a corresponding rotation of said first pulley;

a belt portion operably associated with said first pulley such that rotation of said first pulley causes a corresponding movement of said belt; and a second pulley operably associated with said belt such that movement of said belt causes a corresponding rotation of said second pulley, wherein said positionable portion is fixedly attached to said belt portion such that movement of said belt portion causes a corresponding movement of said positionable portion.

16. A fraction collector according to claim 15 further comprising a support shaft parallel to said lead screw, wherein said carriage portion is slidably engaged with said support shaft for movement along a length thereof, and wherein said rear portion has a third through-hole through which at least a portion of said support shaft extends.

17. A device fraction collector according to claim 16 wherein said dispenser is adapted to extract a fluid sample from a receptacle in addition to delivering a fluid sample thereto.

18. A device for positioning a component thereof along x- and y-axes comprising:

a first motor fixedly attached to said device;

a lead screw coupled to said first motor and extending along a first axis of said device;

a carriage portion threadably engaged with said lead screw so that rotation of said lead screw by said first motor moves said carriage portion along said first axis;

a shaft portion fixedly attached to said carriage and defining a second axis of said device, said second axis being perpendicular to said first axis;

a second motor fixedly attached to said device;

a keyed shaft coupled to said second motor and extending along said first axis;

a first pulley through which said keyed shaft extends in a keyed manner, said carriage portion and said first pulley being slidingly engaged with said keyed shaft for movement along said first axis by rotation of said lead screw by said first motor;

a second pulley carried by said carrier, said second pulley being operably associated with said first pulley by a belt along said second axis so that rotation of said keyed shaft by said second motor translates into movement of said belt; and a positionable portion slidingly attached to said keyed shaft portion and fixedly attached to said belt such that movement of said belt causes a corresponding movement of said positionable portion along said second axis.

19. A device according to claim 18 wherein said positionable portion comprises a dispenser for dispensing a fraction of a fluid sample into a receptacle.

20. A device according to claim 19 wherein said dispenser is adapted to extract a fluid sample from a receptacle in addition to delivering a fluid sample thereto.

21. A device according to claim 18 further comprising a support shaft parallel to said lead screw, wherein said carriage portion is slidably engaged with said support shaft for movement along said first axis.

22. A device according to claim 18 further comprising a rear portion to which said first and second motors are fixedly attached, said rear portion having a first through-hole through at least a portion of which said lead screw extends, and said rear portion further having a second through-hole through at least a portion of which said keyed shaft extends.

23. A device according to claim 22 further comprising a support shaft parallel to said lead screw, wherein said carriage portion is slidably engaged with said support shaft for movement along said first axis, and wherein said rear portion has a third through-hole through which at least a portion of said support shaft extends.

24. A device according to claim 23 further comprising a first forward support having a first through-hole through at least a portion of which said lead screw extends, said first forward support further having a second through-hole through at least a portion of which said support shaft extends, said first forward support being portioned at a distal end of said lead screw and a distal end of said support shaft with respect to said rear portion.

25. A device according to claim 24 further comprising a second forward support having a through-hole through at least a portion of which said keyed shaft extends, said second forward support being positioned at a distal end of said keyed shaft with respect to said rear portion.

26. A device according to claim 25 further comprising a base portion fixedly attached to said rear portion and extending away therefrom, said base portion also fixedly attached to said first and second forward support portions.

* * * * *